United States Patent
Levy et al.

(10) Patent No.: US 10,307,619 B2
(45) Date of Patent: Jun. 4, 2019

(54) REFERENCE-LIBRARY EXTENSION DURING IMAGING OF MOVING ORGANS

(71) Applicants: INSIGHTEC, LTD., Tirat Carmel (IL); Yoav Levy, Hinanit (IL); Yoav Medan, Haifa (IL)

(72) Inventors: Yoav Levy, Hinanit (IL); Yoav Medan, Haifa (IL)

(73) Assignee: INSIGHTEC, LTD., Tirat Carmel (IL)

(*) Notice: Subject to any disclaimer, the term of this patent is extended or adjusted under 35 U.S.C. 154(b) by 1061 days.

(21) Appl. No.: 14/377,063

(22) PCT Filed: Feb. 6, 2013

(86) PCT No.: PCT/IB2013/000345
§ 371 (c)(1),
(2) Date: Aug. 6, 2014

(87) PCT Pub. No.: WO2013/117992
PCT Pub. Date: Aug. 15, 2013

(65) Prior Publication Data
US 2015/0025360 A1    Jan. 22, 2015

Related U.S. Application Data

(60) Provisional application No. 61/595,341, filed on Feb. 6, 2012, provisional application No. 61/595,338, filed on Feb. 6, 2012.

(51) Int. Cl.
*A61B 5/055* (2006.01)
*A61B 5/01* (2006.01)
(Continued)

(52) U.S. Cl.
CPC ............ *A61N 7/00* (2013.01); *A61B 5/055* (2013.01); *A61N 7/02* (2013.01); *G06T 7/248* (2017.01);
(Continued)

(58) Field of Classification Search
CPC ................................ A61B 5/055; A61N 7/02
See application file for complete search history.

(56) References Cited

U.S. PATENT DOCUMENTS

2004/0114791 A1*  6/2004  Atkinson ......... G01R 33/56509
                                                    382/131
2007/0239062 A1* 10/2007  Chopra .................... A61B 5/01
                                                    600/549
(Continued)

FOREIGN PATENT DOCUMENTS

WO    2007008528 A2   1/2007
WO    2009044276 A2   4/2009

OTHER PUBLICATIONS

"MRI-guided focused ultrasound treatments" by K. Hynynen. Ultrasonics. 50 (2010) p. 221-229.*

(Continued)

*Primary Examiner* — Tse W Chen
*Assistant Examiner* — Jason M Ip
(74) *Attorney, Agent, or Firm* — Morgan, Lewis & Bockius LLP

(57) ABSTRACT

Images acquired during an image-guided treatment procedure sometimes exceed the scope of a reference library previously acquired for the purpose of monitoring and/or adjusting the treatment. In this situation, the reference library may be extended dynamically and/or in real time based on the newly acquired treatment images and/or other available information.

41 Claims, 5 Drawing Sheets

(51) Int. Cl.
  *A61N 7/00* (2006.01)
  *A61N 7/02* (2006.01)
  *G06T 7/73* (2017.01)
  *G06T 7/246* (2017.01)
  *A61B 17/00* (2006.01)
  *A61B 90/00* (2016.01)

(52) U.S. Cl.
  CPC ............... *G06T 7/74* (2017.01); *A61B 5/015* (2013.01); *A61B 2017/00084* (2013.01); *A61B 2090/374* (2016.02); *A61N 2007/0056* (2013.01); *F04C 2270/041* (2013.01); *G06T 2207/10088* (2013.01); *G06T 2207/10132* (2013.01); *G06T 2207/30004* (2013.01); *G06T 2207/30096* (2013.01)

(56) References Cited

U.S. PATENT DOCUMENTS

| | | | |
|---|---|---|---|
| 2009/0131782 A1* | 5/2009 | Moonen | A61N 7/02 600/411 |
| 2010/0061596 A1 | 3/2010 | Mostafavi et al. | |
| 2010/0167251 A1* | 7/2010 | Boutchko | A61B 5/416 434/267 |
| 2010/0185081 A1* | 7/2010 | Soher | G01R 33/4804 600/412 |
| 2011/0109309 A1 | 5/2011 | Levy et al. | |

OTHER PUBLICATIONS

International Patent Application No. PCT/IB2013/000345, International Preliminary Report on Patentability dated Aug. 21, 2014, 9 pages.

International Patent Application No. PCT/IB2013/000345, International Search Report and Written Opinion dated Jul. 2, 2013, 13 pages.

Lin, Chun-Ting Justin, "A 0-1 Control Mechanism with Partial Information for Periodic Tumour Motion Classification", IEEE International Symposium on Intelligent Control (ISIC), Part of 2010 IEEE Multi-Conference on Systems and Control, Sep. 8-10, 2010, pp. 1281-1286.

Cui et al., "Multiple Template-Based Fluoroscopic Tracking of Lung Tumor Mass Without Implanted Fiducial Markers", Physics in Medicine and Biology, vol. 52, 2007, pp. 6229-6242.

De Senneville et al., "Atlas-Based Motion Correction for On-Line MR Temperature Mapping", International Conference on Image Processing, vol. 4, 2004, pp. 2571-2574.

European Examination Report for Application No. 13 717 851.3, dated Jun. 1, 2015, 6 pages.

Japanese Official Action for Application No. 2014-555335, dated Nov. 7, 2016, 3 pages.

\* cited by examiner

REFERENCE-LIBRARY EXTENSION DURING IMAGING OF MOVING ORGANS

CROSS-REFERENCE TO RELATED APPLICATION

This application is a U.S. National Phase Application of PCT/IB2013/000345, filed Feb. 6, 2013, which claims priority to and the benefit of, and incorporates by reference herein in their entireties, U.S. Provisional Patent Applications No. 61/595,338 and No. 61/595,341, both filed on Feb. 6, 2012. Reference is also made to the PCT Application of PCT/IB2013/000321, entitled "Reference-Based Motion Tracking During Non-Invasive Therapy," filed on Feb. 6, 2013.

FIELD OF THE INVENTION

The present invention relates to reference-based imaging applications and, in particular, to reference-based magnetic resonance imaging (MRI). Various embodiments concern motion compensation for purposes of thermometry or organ tracking in image-guided non-invasive therapy.

BACKGROUND

Magnetic resonance (MR) imaging of internal body tissues may be used for numerous medical procedures, including diagnosis and surgery. Generally, an MRI system 100, as depicted in FIG. 1, includes a static-field magnet 102, one or more gradient-field coils 104, a radio-frequency (RF) transmitter 106, and an RF receiver (not shown). (In some embodiments, the same device is used alternately as RF transmitter or receiver.) The magnet includes a region 108 for receiving a patient 110 therein, and provides a static, relatively homogeneous magnetic field over the patient, which causes hydrogen nuclei spins to align with and precess about the general direction of the magnetic field. The spin alignment creates a net magnetization in the tissue that depends, generally, on the type of tissue and can, thus, be used to create contrast in an MR image. Time-variable magnetic field gradients generated by the gradient-field coils 104 are superposed with the static magnetic field so as to encode spatial information by spatio-temporally varying the precession frequency of the spins. The RF transmitter 106 transmits RF pulse sequences over the patient 110 to cause some of the aligned spins to alternate between a temporary high-energy non-aligned state and the aligned state, thereby inducing an RF response signal called the MR echo or MR response signal. To obtain an MR image, the MR response signal is integrated over the entire (two- or three-dimensional) imaging region and sampled by the RF receiver to produce a time series of response signals that constitute the raw image data. This raw data is passed on to a computation unit 112. Each data point in the time series can be interpreted as the value of the Fourier transform of the position-dependent local magnetization at a particular point in k-space (i.e., wavevector space), where the wavevector k is a function of the time development of the gradient fields. Thus, by Fourier-transforming the time series of the response signal, the computation unit 112 can reconstruct a real-space image of the tissue (i.e., an image showing the measured magnetization-affecting tissue properties as a function of spatial coordinates) from the raw data. The real-space MR image may then be displayed to the user.

The MRI system 100 may be used to plan a medical procedure as well as to assist in locating and guiding medical instruments and monitor treatment progress during the procedure. For example, a medical procedure can be performed on a patient using a medical instrument while the patient is in the MRI machine. The medical instrument may be inserted into the patient, or used non-invasively, i.e., placed externally to the patient while creating a therapeutic or diagnostic effect in the tissue. MRI may be used to image an anatomical region of the patient, locate a treatment target within the region, monitor the location of the medical instrument (or the focus of its effects) relative to the target (preferably in real time), and/or monitor the temperature in and surrounding the target tissue.

For instance, the medical instrument can be a focused ultrasound device 114 that is located outside a patient's body and focuses ultrasonic energy into the patient's body. Ultrasound penetrates well through soft tissues and, due to its short wavelengths, can be focused to spots with dimensions of a few millimeters; therefore, it can be used for highly localized non-invasive surgery—for example, to ablate, coagulate, or otherwise necrose cancerous tissue without causing significant damage to surrounding healthy tissue. An ultrasound focusing system generally utilizes an acoustic transducer surface, or an array of transducer surfaces, to generate an ultrasound beam. The transducer may be geometrically shaped and positioned such that the ultrasonic energy is focused at a "focal zone" corresponding to the target tissue mass within the patient. During wave propagation through the tissue, a portion of the ultrasound energy is absorbed, leading to increased temperature and, eventually, to cellular necrosis—preferably at the target tissue mass in the focal zone. The individual surfaces, or "elements," of the transducer array are typically individually controllable, i.e., their phases and/or amplitudes can be set independently of one another (e.g., using a "beamformer" with suitable delay and amplifier circuitry for the elements), allowing the beam to be steered in a desired direction, focused at a desired distance, and its beam profile to be conformed to a desired shape. Thus, the focal zone can be rapidly displaced and/or reshaped by independently adjusting the amplitudes and phases of the electrical signal input into the transducer elements; the transducer elements, in other words, are operable as a phased array.

During MR-guided focused-ultrasound (MRgFUS) treatment, patient motion (such as periodic motion due to respiration or random movements) can pose a considerable challenge to therapeutic efficacy and safety. Compensation for motion is necessary to ensure that the ultrasound beam remains focused on the target and does not damage the surrounding healthy tissues. In MRgFUS systems, motion compensation is generally accomplished by tracking the target in the images and steering the ultrasound beam based on the tracked position. One approach to target tracking involves directly determining the coordinates of the target, or of easier identifiable "anatomical landmarks" at fixed locations relative to the target, in the images. In an alternative approach, the relative shifts between successive images are determined by correlating one image with a large number of computationally shifted copies of the other image, and selecting the shifted image that provides the best match. In either case, significant image-processing time is expended to determine the target location. Thus, if such image processing is performed on the images acquired during treatment, the effective imaging rate is typically increased significantly, often impeding real-time motion compensation. This may cause beam-targeting inaccuracies and/or necessitate treatment interruption to correct for any misalignment due to displacement of the target tissue or organ.

To avoid these problems and facilitate target tracking in real time, a library of reference images covering different stages within the anticipated range of patient motion may be acquired and analyzed prior to treatment. The location of the target (or other object of interest) within each reference image is stored along or in association with the respective image, e.g., in an integrated reference record. As actual treatment proceeds, the images acquired in real time are correlated against the reference images in the library to determine matches based on image similarity. The location of the target region in the acquired treatment image is then inferred from the locational information associated with the corresponding reference image. Because image matching is, generally, computationally less involved then detecting and localizing objects within an image, this approach can achieve significant savings in processing time during treatment, thus facilitating real-time tracking.

Motion compensation is also relevant in MR-based thermometry (i.e., the generation of temperature maps of a monitored anatomical region from MR images thereof), where it can likewise benefit from a reference library acquired prior to treatment. Thermometry facilitates monitoring the progress of thermal treatment of target tissue, e.g., to ensure that non-target tissues are not inadvertently heated beyond clinically tolerable levels. Among various methods available for MR thermometry, the proton resonance frequency (PRF) shift method is often optimal due to its excellent linearity with respect to temperature change, near-independence from tissue type, and temperature map acquisition with high spatial and temporal resolution. The PRF shift method is based on the phenomenon that the MR resonance frequency of protons in water molecules changes linearly with temperature (with a constant of proportionality that, advantageously, is relatively constant between tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline (or reference) PRF phase image prior to a temperature change and then to acquire a second phase image—i.e., a treatment image—after the temperature change, thereby capturing a small phase change that is proportional to the change in temperature. A map of temperature changes may then be computed from the (reconstructed, i.e., real-space) images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo). Further, if the temperature distribution in the imaged area at the time of acquisition of the baseline image is known, the temperature-difference map can be added to that baseline temperature in order to obtain the absolute-temperature distribution corresponding to the treatment image.

The ability to obtain a temperature (difference) map for a treatment image depends on the existence of a suitable reference image, i.e., an image that, up to the temperature distribution, reflects the imaging conditions, including the location of the object(s) of interest, as they exist at the time the treatment image is acquired. If the region of interest is stationary (as are, typically, e.g., the prostate and uterine tract), a single reference (or baseline) image may suffice. Typically, however, the patient—and with him the region to be monitored or one or more organs therein—moves during treatment; such motion can be periodic (e.g., due to respiration) or sporadic and random. In this case, a library of reference images covering the range of motion may be acquired prior to treatment (e.g., heating), and an absolute-temperature map may optionally be stored along with each reference image (e.g., forming a reference record including the MR image and temperature map for each stage of motion). To obtain the proper reference (or baseline) image for a new treatment image, a correlation or other suitable image-selection technique is performed against the library to find the baseline image best aligned, spatially, with the treatment image. The selected baseline image and treatment image are processed as described above to determine the changes in temperature, and an absolute-temperature map for the treatment image is computed based on the temperature map corresponding to the baseline image and the image-to-image phase changes. This method is often referred to as multi-baseline thermometry. Additional algorithms (e.g., to account for phase wrapping, to correct for drift in the static magnetic field, or to integrate measurements from multiple resources such as multiple MR channels) may also be applied.

Although thermometry and object tracking for the purpose of beam steering involve very different operations and technical constraints, in both cases, the ability to accommodate movement may be critical, and may depend on the robustness of the reference library. When the patient's movement exceeds what is anticipated (i.e., the target region in the treatment image is no longer in a region covered by the reference library and/or a baseline image is not found because the image similarities between the treatment image and reference images are insufficient), it may be necessary to stop treatment in order to correct misalignment due to displacement of the target tissue or organ. Movements of anatomical structures other than the target can also negate the usefulness of the reference library by disturbing the electromagnetic field (which directly affects the phase map of the image) so that the resulting treatment images do not directly correspond in detail to the reference images. Unless movement and other changes exceeding the coverage of the reference library are transient and brief, treatment must typically be halted to allow for recalibration and realignment of the treatment device and for the acquisition and/or processing of new reference images. The result is inconvenience and delay.

Accordingly, there is a need for the efficient extension of the reference library when reference images do not match newly obtained images (due to movements, changes in imaging parameters, or other factors), preferably so that treatment can be continuously performed without interruption.

SUMMARY

The present invention relates, in various embodiments, to the use of reference libraries in image-guided treatment procedures (or other medical imaging applications), and provides systems and methods for extending the library dynamically and, preferably, in real-time during treatment when necessary, i.e., when no suitable reference image can be found in the library for a given treatment image. Such reference library extension increases the flexibility of reference-based imaging and facilitates uninterrupted treatment, or at least minimizes delays, in many cases that would otherwise require the termination of a treatment procedure.

The reference library includes a plurality of reference images (e.g., MR images) and, typically, additional application-specific data associated with each image (such as the location of an object of interest therein for motion-tracking applications, or an absolute-temperature map associated therewith for thermometry applications). Hereinafter, a reference image and its associated data are collectively referred to as a "reference image record" or simply a "reference record," regardless of whether the image and associated data are stored in an integrated data file (or multiple files) or in different data structures and/or at different memory locations (in which case an additional database may link each image with the associated information). The images may, e.g., be MR images, ultrasound images, X-ray images, X-Ray computer-tomography (CT) images, or other images. Further, unless otherwise apparent from context, the term "images," as used herein, may refer to real-space images (e.g., reconstructed MR images), the raw data from which they are derived (e.g., k-space MR images or CT projection images), or both.

The initial reference library is generally acquired prior to treatment. Subsequently, as the anatomical region of interest is repeatedly imaged during treatment, the reference library is searched for reference images matching the series of treatment images; the treatment images and corresponding reference image records together are used to guide and/or monitor the treatment. If unanticipated movements or changes in imaging conditions are encountered during treatment and, consequently, no matching reference image is found, the treatment image (or an image derived therefrom) is incorporated into the reference library as a new reference image. Further, any additional information required to form a complete reference record for the application at hand is derived or estimated from or based on the current and/or one or more prior treatment images (optionally in combination with a physical model) and added to the reference library in association with the new reference image. Subsequent treatment images are then compared against the expanded reference library. The process is iterated, and whenever no suitable reference image is identified, the library is supplemented based on the instant treatment image, and treatment proceeds unless a termination condition imposed for safety purposes triggers early termination. (A termination condition may, e.g., specify, the maximum allowable number of successive treatment images falling outside the initial reference library.) The reference library is, thus, dynamically extended during treatment, usually obviating the need to interrupt treatment.

Accordingly, in one aspect, the invention provides a method for monitoring an anatomical region during treatment thereof. Prior to the treatment, a library of reference image records of the anatomical region is established; each reference image record includes a reference image and, in some embodiments, data associated with the reference image. During the treatment, treatment images of the anatomical region are repeatedly acquired. For each treatment image, it is determined whether a reference image from the library matches the acquired treatment image according to an image-similarity criterion, and if none of the reference images in the library matches the acquired treatment image according to the image-similarity criterion, the reference library is extended based (at least in part) on the acquired treatment image and/or a previous treatment image by adding a new reference image record including a new reference image (which, in some embodiments, satisfies the image-similarity criterion with respect to the treatment image) to the library. The anatomical region is monitored based at least in part on the acquired treatment images and the reference library. In some embodiments, the method further includes modifying parameters associated with the treatment (e.g., the treatment energy, the treatment power, the treatment beam shape, or the targeted area) based at least in part on the monitoring, and/or changing imaging parameters during the treatment.

Extending the reference library may include adding the treatment image, or an image derived from the treatment image, to the library as the new reference image. Alternatively, in some embodiments, the reference library may be extended by estimating the motion of an object of interest in the anatomical region based on at least one of the treatment image or the previous image, acquiring a new treatment image encompassing the object of interest based on the estimated motion, and adding the new treatment image to the library as the new reference image. Extending the reference library may further include deriving corresponding data for the new reference image and adding it to the library in association therewith. In some embodiments, the library is initially empty of reference images. In other embodiments, the library initially contains a plurality of reference images each corresponding to a different stage of motion of the anatomical region.

In some embodiments, the data associated with the different reference images includes respective locations of one or more objects of interest (e.g., a treatment target and/or non-target tissues or organs sensitive to therapeutic energy) therein. Monitoring the anatomical region may involve monitoring the location(s) of the object(s) of interest based on the locations stored in association with reference images matching the acquired treatment images. The treatment may include the application of a therapeutic energy beam to the target; based on the monitored location(s) of the target and/or sensitive organs, the beam may be adjusted. The location of the object of interest in a new reference image may be derived from the treatment image using image analysis. Alternatively, the location of the object of interest in the new reference image may be derived from one or more previous treatment images and a physical model characterizing motion of the object of interest.

In some embodiments, the data associated with the reference images includes thermal maps corresponding thereto. The method may involve monitoring a temperature change within the anatomical region based on phase differences between the acquired treatment images and the matching reference images; the absolute temperature within the anatomical region may be monitored based, further, on the thermal maps stored in association with the reference images matching the acquired treatment images. The thermal map corresponding to a new reference image may be derived from one or more thermal maps corresponding to one or more previous treatment images, optionally based, further, on a physical model (which may, e.g., characterize motion of the monitored anatomical region, or the temperature evolution within the region). The method may further involve establishing a thermal map of the anatomical region after treatment, and retroactively adjusting the monitored absolute temperature during treatment based thereon.

In another aspect, the invention is directed to a system for monitoring an anatomical region during treatment thereof. The system includes an imaging apparatus for imaging the anatomical region, memory for storing a library of reference image records comprising reference images of the anatomical region, and a computation unit. The computation unit is configured to (i) repeatedly cause the imaging apparatus to acquire a treatment image of the anatomical region during the treatment, (ii) determine whether any of the reference images in the library matches the acquired treatment image according to an image-similarity criterion, (iii) if none of the reference images in the library matches the acquired treatment image, extend the reference library based, at least in part, on at least one of the acquired treatment image or a previous treatment image by adding a new reference image record comprising a new reference image to the library, and (iv) monitor the anatomical region based at least in part on the acquired treatment images and the reference library. The system may also include an ultrasound transducer array for focusing a therapeutic energy beam onto a target in the anatomical region, and the computation unit may be configured to adjust the beam based on the monitoring.

Each reference image record may include data associated with the reference image of the respective record, and the computation unit may be configured to derive data corresponding to the new reference image and adding it to the library in association therewith. In some embodiments, the data associated with the reference images include respective locations of one or more objects of interest therein. The computation unit may be configured to monitor the location(s) of the object(s) of interest based on the locations stored in association with reference images matching the acquired treatment images; the treatment may be adjusted based on the monitored locations. In some embodiments, the data associated with the reference images comprises thermal maps corresponding thereto. The computation unit may be configured to monitor an absolute temperature in the anatomical region based on phase differences between the acquired treatment images and matching reference images and on the thermal maps stored in association with the matching reference images.

BRIEF DESCRIPTION OF THE DRAWINGS

The foregoing will be more readily understood from the following detailed description of the invention, in particular, when read in conjunction with the drawings, in which.

DETAILED DESCRIPTION

The present invention relates generally to systems and methods for imaging an anatomical region within a patient, typically in conjunction with treatment thereof, and in particular to reference-based imaging that facilitates compensating for patient motion, changes in the treatment configuration or imaging parameters (e.g., the scan field), or other factors affecting the processing and analysis of the acquired images. In contrast to conventional methods, where the reference-image library is generally not updated once treatment has commenced, the instant invention provides methods for dynamically extending the reference library during treatment if needed. For definiteness, the following description refers specifically to MR imaging applications. It should be understood, however, that the concepts and features discussed herein are applicable to other imaging modalities as well.

Figure 2:
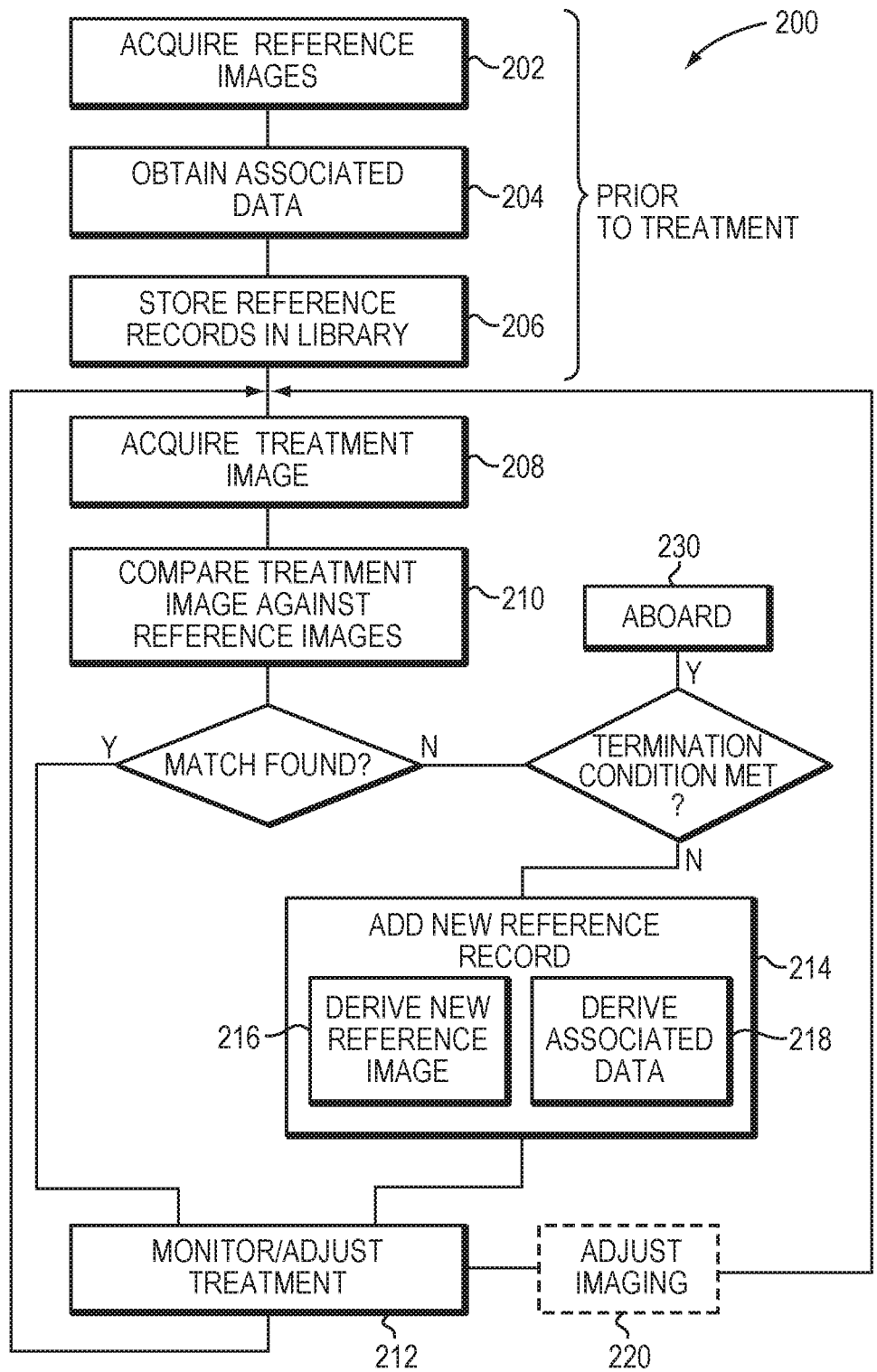
FIG. 2 is a flow chart illustrating reference-library extension in accordance with various embodiments.

Refer to FIG. 2, which conceptually illustrates a method 200 for reference-library extension in accordance with various embodiments. The method 200 involves, prior to treatment, acquiring a plurality of reference images of an imaging region including the anatomical region of interest (step 202). The reference images may cover an anticipated range of motion of the anatomical region or objects and tissues therein, with each image corresponding to a different stage of motion (e.g., a different stage in a respiratory cycle). Alternatively or additionally, the reference images may be acquired under different imaging conditions and/or treatment configurations, and may, generally, correspond to different phase backgrounds resulting from various factors. For many applications, the method further involves deriving or otherwise obtaining additional information associated with each image (step 204). For instance, if the library serves to track the motion of a treatment target or other object of interest in real time, the location of the object of interest in each reference image may be stored along with the image. In thermometry applications, the reference library may provide baseline images for background subtraction that cover a range of expected phase backgrounds (e.g., resulting from movements of or within the region to be monitored, or from other phase-affecting conditions that are not temperature-related), and each image may have an absolute-temperature map associated therewith. (FIGS. 3 and 4, discussed further below, illustrate in more detail the application of the method 200 to target tracking and thermometry, respectively.) The reference images and associated data are stored as reference records in a reference library (step 206).

During treatment, the anatomical region is repeatedly imaged (step 208), and each treatment image is compared against the reference library based on image similarity to determine whether any of the reference images matches the treatment image (step 210). The comparison may generally be based on real-space or k-space image data, i.e., it may involve, but does not necessarily require, the reconstruction of real-space treatment images from the raw data acquired during treatment. Further, it may suffice to compare portions of the images. Typically, the comparison is performed on a pixel-by-pixel basis, where a "pixel" refers to an element of the image data array, which generally stores amplitude and phase values as a function of real-space coordinates or k-space coordinates. Suitable similarity metrics include, for example, cross-correlation coefficients, the sum of squared intensity differences, mutual information (as the term is used in probability and information theory), ratio-image uniformity (i.e., the normalized standard deviation of the ratio of corresponding pixel values), the mean squared error, the sum of absolute differences, the sum of squared errors, the sum of absolute transformed differences (which uses a Hadamard or other frequency transform of the differences between corresponding pixels in the two images), or complex cross-correlation (for complex images, such as MRI images), and other techniques familiar, to those of skill in the art, in connection with image registration. In addition, in some embodiments, the treatment image is compared against the reference library based on meta-data such as scan parameters or other external information (e.g., the state of a respiratory monitoring belt). Accordingly, as used herein, the term "image similarity" broadly connotes similarity based on any suitable metric (as described above) and/or on meta-data associated with the image.

The determination whether a match exists is based on a specified image-similarity criterion. For example, the similarity between the treatment image and the closest reference image, as measured by the chosen similarity metric, may be compared against a (metric-specific) similarity threshold, and only if the level of similarity surpasses that of the threshold (which typically means, for metrics that measure the differences, i.e., the dissimilarity, between images, that the value of the metric falls below the threshold value) is the reference image considered a match for the treatment image. If a matching reference image is found, treatment proceeds in the conventional manner, using the treatment image and the corresponding reference image record as applicable to monitor and/or adjust the treatment (step 212) (see, e.g., FIGS. 3 and 4).

If none of the reference images in the library matches the acquired treatment image according to the applied image-similarity criterion, the reference library is supplemented with a new reference image record (step 214). This extension usually involves two steps: First, a new reference image that satisfies the image-similarity criterion with respect to the treatment image is added to the library (step 216). In the simplest case, the treatment image itself may be used as the new reference image; the image-similarity criterion is then trivially satisfied. Sometimes, however, the treatment image is further processed to yield a suitable reference image. For example, hot spots resulting from the treatment may be removed from the image so as to leave a phase background unrelated to the treatment. Outside the hot-spot area, the treatment image and the new reference image will still be the same, ensuring satisfaction of the similarity criterion. Furthermore, if the treatment target (or other object of interest) has moved outside the imaged region, the scan field itself may be shifted (by changing suitable imaging parameters) to re-capture the target (or other object), and a new treatment image may be acquired at the new position and added as a new reference image to the library. In some embodiments, treatment images subsequently acquired at the new position are compared with the newly added reference image(s) obtained at the same position. Generally, the treatment images may be matched to the references based on similarity and, in some cases, meta-data such as scan parameters or other external information (e.g., the state of a respiratory monitoring belt). The requisite shift in the scan field may be lateral if the target has moved in-plane, or to a new imaging plane if the target has moved out-of-plane. Second, application-specific data associated with the new reference image is derived based on the treatment image, one or more previously acquired treatment images, existing reference records, and/or other available information (such as a model of the target motion) (step 218) and stored along with the new reference image. The data associated with the new reference record may then be used, along with the treatment image to which it corresponds, to monitor and/or adjust the treatment (step 212). In certain circumstances, the imaging process itself is also adjusted via one or more imaging parameters (step 220), e.g., to retain the scan field around the current target position or to optimize image contrast. Similarly, other monitoring parameters, such as the frequency of image acquisition, may be adjusted, e.g., to conserve scarce computational resources by imaging at a rate commensurate with motion and other changes within the monitored region.

Using the current reference library as the starting point (whether it has been extended or not), image acquisition and matching against the reference library (steps 208, 210), treatment monitoring and adjustment (212), and, if necessary, extension of the reference library (step 214) are then repeated. As new reference records are added to the library based on treatment images not covered by the original library, the library may continue to grow. Alternatively, in some embodiments, old reference images may be removed from the library if it becomes clear that they are obsolete, e.g., because movement of the target back into the originally covered area becomes unlikely.

In principle, the process can be repeated indefinitely, or until treatment is complete. If the treatment images deviate too much (or for too long) from the scope of the original library, however, it may be desirable to terminate the procedure prematurely for safety reasons (step 230). For example, if several successive treatment images cannot be matched against any of the reference images, requiring repeated estimates of treatment-relevant information (such as the location of the treatment target), the uncertainty associated with these estimates may increase beyond a tolerable level. Similarly, a tracked organ may move too far outside the anticipated range of motion, or imaging parameters may exceed their expected ranges by too much. Further, in some instances it may not be possible to derive the required application-specific data associated with the new reference image from the treatment image. In all of these scenarios, rather than continuing treatment despite the risk of significant treatment inaccuracies, it may be preferable to abort the treatment procedure, recalibrate the system and acquire a new reference library off-line, and resume the treatment thereafter, as is done conventionally. Conversely, if, following extension of the reference library during one iteration, treatment images return to the range covered by the original library, the intercedently derived reference records may be revised retroactively based on the new treatment images. For example, a target location extrapolated for a non-covered treatment image from the successive locations associated with a preceding series of covered treatment images may be corrected or further refined based on a subsequent covered treatment image.

Figure 3:
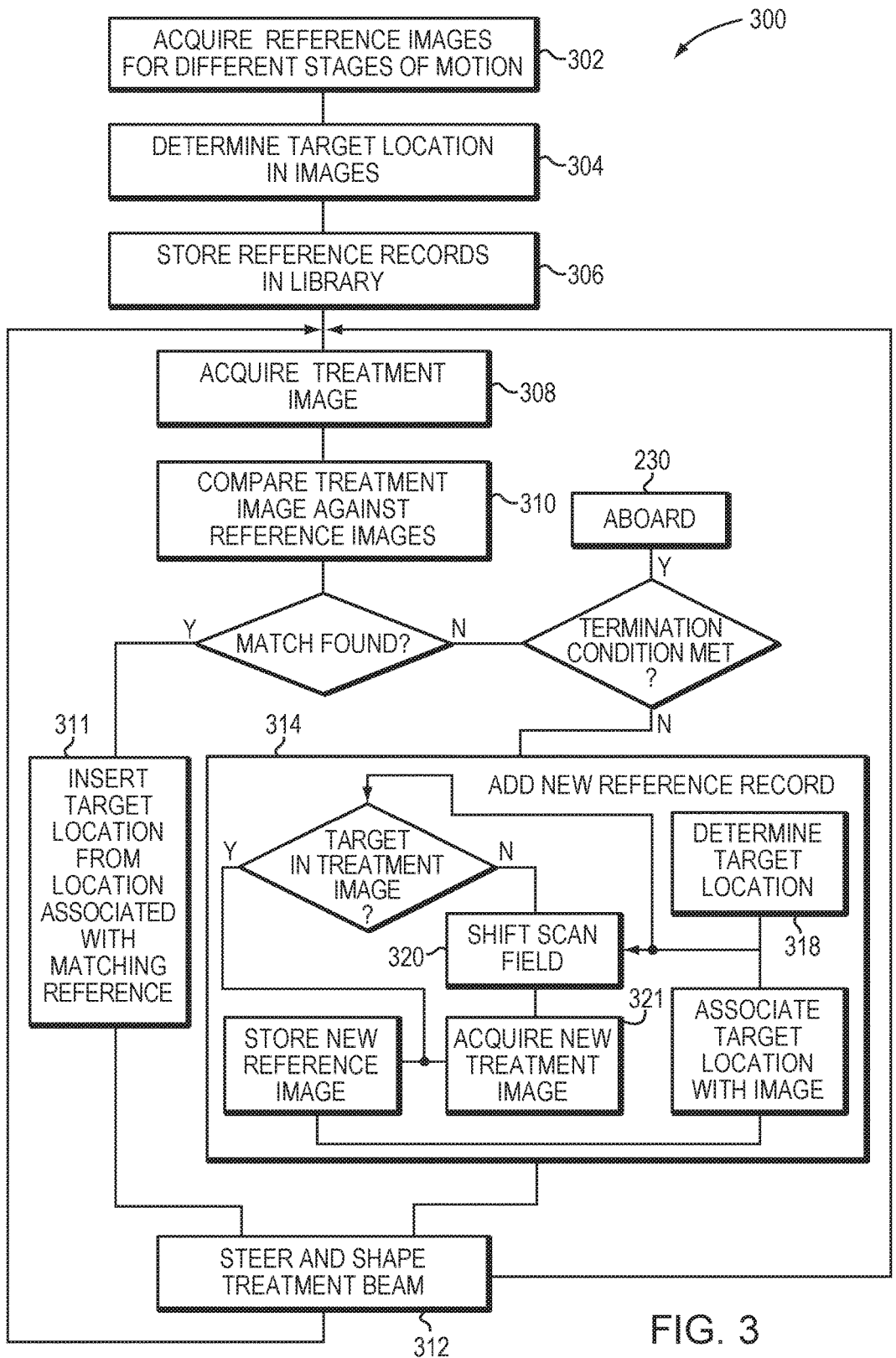
FIG. 3 is a flow chart illustrating reference-library extension for image-guided beam-focusing applications in accordance with various embodiments.

FIG. 3 illustrates reference-library extension in the context of real-time tracking of a treatment target or other anatomical object of interest during treatment thereof The treatment may involve, for example, the application of focused ultrasound to (i.e., the sonication of) a tissue or organ for the purpose of heating it, either to necrose, ablate, or otherwise destroy the tissue if it is, e.g., cancerous, or for non-destructive treatments such as pain amelioration or the controlled inducement of hyperthermia. Ultrasound may also be used for other, nonthermal types of treatment, such as, e.g., neuromodulation. Alternatively, the treatment may involve other treatment modalities using different forms of therapeutic energy, such as, e.g., radio-frequency (RF) radiation, X-rays or gamma rays, or charged particles. Motion tracking during the treatment may serve to guide the therapeutic energy beam onto the target and/or around other, non-target tissues and organs, i.e., to adjust the beam focus, profile, and/or direction based on images of the affected anatomical region. For definiteness and ease of illustration, the following discussion refers specifically to target tracking during focused-ultrasound treatment; it is to be understood, however, that the described method applies similarly to different forms of therapeutic energy and different objects of interest.

For target-tracking purposes, the method 300 begins with acquiring a reference library that covers different stages during an anticipated range of target motion (step 302), and processing the individual reference images to determine the location of the target therein (step 304). Typically, this step 304 is performed on real-space images reconstructed from the MR raw (i.e., k-space) data, using any of a variety of feature-detection or tracking methods known to those of skill in the art, including, without limitation, edge or blob detection to identify the target itself or an anatomical landmark fixedly positioned relative thereto; block-matching algorithms, phase-correlation, optical-flow methods, or other direct, pixel-based methods to determine motion vectors (or relative changes in the target or landmark locations) between different images; and/or indirect, feature-based methods for matching corresponding features between images. The locational information extracted from each reference image (in step 304) is stored along with the image in a reference image record (step 306).

During treatment, the anatomical region of interest including the (generally moving) target is monitored by repeatedly imaging the region (step 308), matching each treatment image, if possible, with one of the reference images in the library by applying a similarity criterion to the real-space or k-space image data (or a portion thereof) (step 310), and inferring the target location from the locational information stored with the selected reference image (step 311). Based on the target location thus determined, the beam focus can then be steered onto the target (step 312), and the process continues with the acquisition of the next treatment image (step 308).

If a newly obtained treatment image does not correspond to any of the reference images contained in the library—e.g., the similarity between the new image and reference images in the library is below (or the dissimilarity is above) a predetermined threshold—the location of the target in the new image is established by other means (step 318). For example, if the target is still within the new treatment image, just not in the region of motion covered by the initial reference library, the same methods as are used to determine the target location in the reference images (in step 304) may be employed. While this computational process may take too long to allow treatment to continue without delay, the target location, once computed, is stored along with the treatment image as a new reference record in the library such that, the next time the target is encountered in the same or a similar position, the treatment procedure will benefit in real-time from the previous computation.

Even if the target has moved outside the field of the treatment image altogether, it may be possible to derive its location from the treatment image if the anatomical region covered by the treatment image overlaps (appreciably—e.g., more than ⅓ or, in some embodiments, more than ½) with at least one of the reference images: using image registration based on the overlapping image portions, the relative shift and deformation of the anatomical region—and thus the target—between the treatment and reference images may be determined. Alternatively, the target movement and/or current target location may be extrapolated from one or more prior treatment images in which the target's location is known. Optionally, such extrapolation may be aided by a physical model of target motion and/or by supplemental measurements of target location using additional equipment such as, e.g., a respiratory monitoring belt. In situations where the target has moved outside the imaged region, the imaging field is steered to encompass the estimated location of the target (step 320), and a new treatment image is obtained (step 321). The location of the target is then associated with the newly obtained treatment image, and both are added to the reference library as a new reference record (step 314). (Alternatively, rather than acquiring a new treatment image for use as a reference image, the new reference image may, in certain embodiments, be calculated.) The new coordinates of the target are now established, and the treatment beam can be steered accordingly (step 312). Further, if the motion of the target (and/or surrounding tissues) is non-rigid such that not only its position and orientation but also its shape has changed, the newly acquired treatment image may be analyzed to determine the target boundaries and shape the focal zone accordingly (also step 312).

Figure 4:
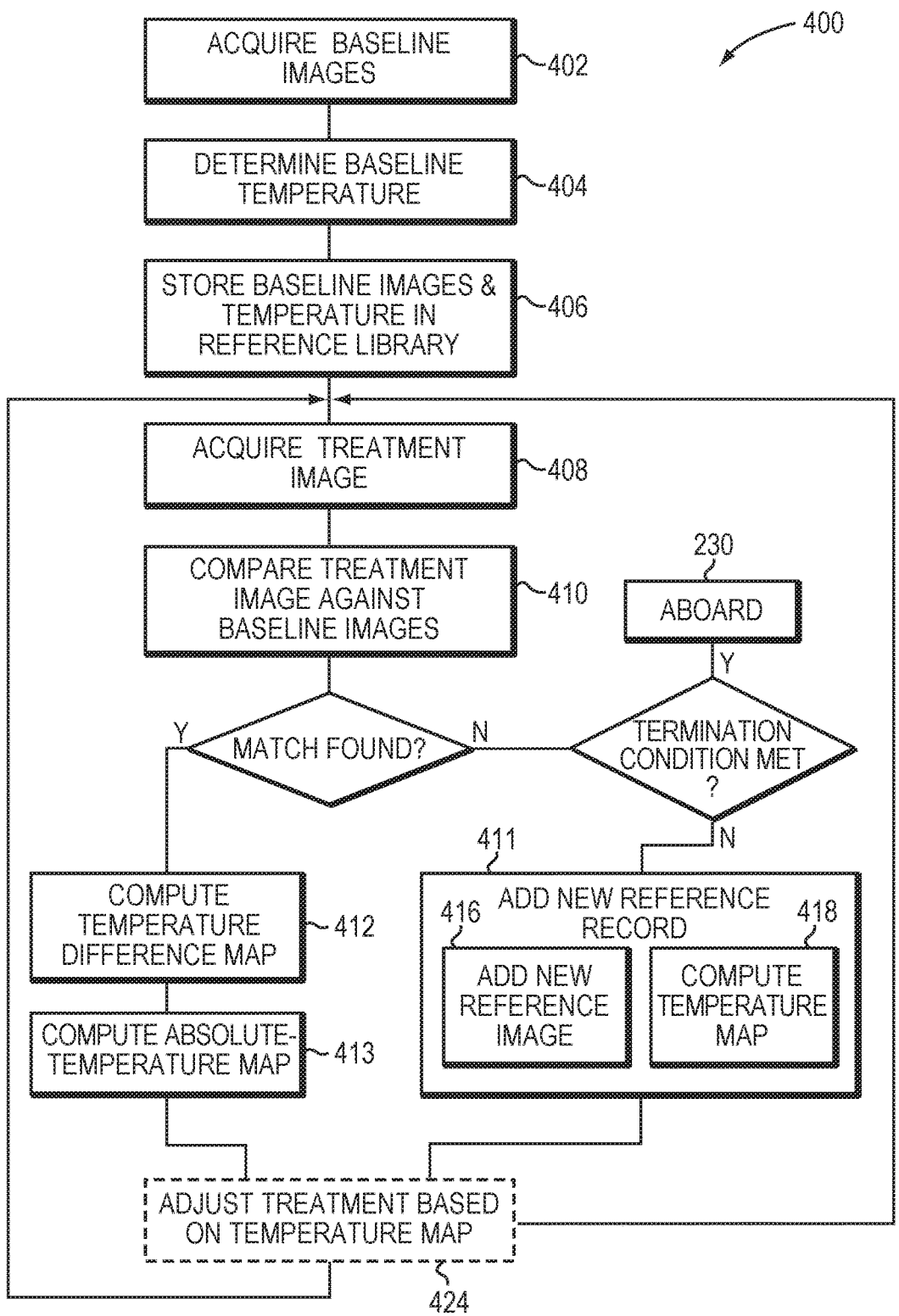
FIG. 4 is a flow chart illustrating reference-library extension for thermometry applications in accordance with various embodiments.

Refer now to FIG. 4, which illustrates a method 400 for reference-library extension in the context of MR thermometry, i.e., repeated image-based measurements of the temperature distribution in an anatomical region of interest (typically for the purpose of monitoring the progress of thermal treatment). The reference images acquired prior to treatment (in step 402) serve, in this application, as baseline images that reflect a phase background independent of the temperature changes caused during the subsequent treatment; these baseline images can be subtracted from corresponding treatment images to extract the temperature-related phase contributions from the latter. Different reference images correspond to different phase backgrounds that can result from different locations of the treatment target itself, from different configurations of the surrounding tissues, the treatment device or other medical devices within or in the vicinity of the imaging region, and/or from other differences in imaging conditions, including a deliberate shift in the scan location (e.g., for the purpose of eliminating artifacts, switching to another target on the fly, monitoring objects of interest in the background of the target, or compensating in advance for predict motion or other events). For example, during a thermal treatment procedure, anatomical constraints may require the treatment device to be moved to a series of different locations relative to the treated anatomical region (e.g., to access different targets or heat a target uniformly from different directions), and the different device locations may affect the image phase background. Thus, even if the treatment target itself does not move, different treatment stages may require different reference images for proper phase background subtraction.

The reference images facilitate computing a map of temperature changes relative to a baseline temperature distribution as it existed at the acquisition time of a references image. To enable absolute-temperature measurements, this baseline temperature distribution may be established for each reference image (step 404) and stored along with the image (step 406). Establishing the baseline temperature may involve, e.g., a simple assumption or a mathematical fit to temperatures directly measured at one or more discrete locations. For example, in many applications, the anatomical region of interest has, prior to treatment, a uniform temperature, e.g., body temperature (37° C.), which constitutes the baseline temperature. In other treatment scenarios, active cooling (or heating) is applied at tissue surfaces, establishing a temperature gradient across the region of interest that can be estimated based on direct temperature measurements at a few selected points.

Once an initial reference library has been compiled, thermal treatment commences. For example, ultrasound may be focused at a target to locally heat the target tissue. In general, the absorbed heat will dissipate into surrounding tissues and increase their temperature at least slightly. The temperature changes within a region encompassing the target can be monitored by imaging the region (step 408), comparing the image against the reference library (step 410) in order to identify a well-registered reference image based on an image-similarity criterion, and processing the matching reference and treatment images to determine a temperature-difference map (step 412). Although the comparison between treatment and reference images to identify a match may in principle be based on k-space or real-space image data, and even on partial images, processing a pair of images for purposes of thermometry typically involves the pixel-wise subtraction of complete real-space images (and subsequent conversion of the phase difference into a temperature-difference map). The absolute-temperature map stored along with the selected reference image (i.e., as part of the selected reference image record) can be added to the temperature-difference map to yield the absolute-temperature distribution corresponding to the treatment image (step 413).

In determining whether a match exists between a reference image and a treatment image, the "hot spot" generated by the treatment is typically disregarded; for example, the heated region may be masked in the images such that the similarity measurements is based solely on the surrounding area (whose temperature is, ideally, stable). In certain embodiments, however, the reference images acquired prior to treatment (in step 402) are deliberately manipulated to reflect the expected temperature increase in the target; in other words, a "fake" phase map is created that is as similar as possible to the treatment image. In this case, a suitable reference for the treatment image can be identified without the need to mask or otherwise compensate for the hot spot.

In instances where no suitable reference image record can be found, a new reference record is added to the library (step 414) based on the instant treatment image (or, if the target has moved outside the image, a new treatment image obtained after the scan field has been shifted to encompass the target, as depicted in FIG. 3), which may be added as is as a new reference image (step 416), and a corresponding temperature distribution that may be computed or estimated from a previous temperature map (or multiple prior temperature maps) using a physical model (step 418). The previous temperature map may be, e.g., the temperature distribution determined from the last treatment image for which a suitable reference image was found or, alternatively, the most recently obtained temperature map, whether it was measured or, itself, computed and/or estimated. The physical model may account for both movement and deformation of the mapped anatomical region (if any) and the temperature evolution in the region since the point in time associated with the previous temperature map, and may be based on theoretical information as well as on treatment images or other measurements taken since the beginning of the treatment procedure.

For example, changes in the location and/or spatial confirmation of the target and surrounding tissues can often be determined from the current treatment image and a previous (e.g., the most recent) treatment image, optionally in conjunction with a physical model that accounts for tissue elasticity and movement constraints. Based on the characterization of the tissue motion and/or deformation between the previous and current treatment images, the temperature map associated with the former may be translated, extrapolated, and/or deformed, by methods known to those of skill in the art, to yield a new temperature map that compensates for the motion and/or deformation. U.S. Ser. No. 13/194,286, filed on Jul. 29, 2011 and hereby incorporated by reference, describes the use of computational models of movement in conjunction with image-based tracking; for example, models characterizing the morphology and behavior of particular organs as are known in the art may be used to interpret or constrain interpretation of the image data. Based on movement parameters dictated by the model, pixels of the temperature map may be shifted to deform the map to approximate movement-related shifts. Alternatively, the new temperature map may be obtained with conventional image-deformation ("morphing") algorithms (e.g., where the shifts are small or tissue characteristics are unlikely to govern movement). In case of an out-of-plane change in the scan location (between the previous and current treatment images), the new thermal map may be "sliced" from a volumetric temperature map estimated from one or more previous temperature maps (e.g., by interpolation between temperature maps corresponding to treatment images simultaneously acquired in imaging planes that bracket the current imaging plane).

Furthermore, the previous temperature map (or a new temperature map derived therefrom to account for tissue movement and deformation) is adjusted to reflect the temperature evolution in the imaged region. For example, changes in temperature resulting from the deliberate application of thermal energy can be computed or estimated based on known treatment parameters (e.g., the intensity and duration of, or the total energy delivered during, a sonication) in conjunction with a model of energy absorption and transport in the tissue. In general, models for temperature evolution may be volumetric, and may use multiple previous temperature maps measured concurrently or sequentially in different imaging planes as input. (For example, temperature measurements may repeatedly cycle through multiple imaging planes.) Further, the evolution of the temperature in a monitored region may be modeled based on temperature measurements (e.g., multiple previous temperature maps) acquired at different times in the past. In any case, the physical model, as applied to the previously obtained temperature map(s), may provide a pixel-by-pixel estimate of the current temperature.

The new estimated temperature map is associated with the current treatment image (which serves as a new reference image) in the reference library. A temperature map for a subsequent treatment image that satisfies the similarity criterion with respect to the new reference image may be generated from the phase differences between the images and the saved temperature map associated with the new reference image. (Alternatively, in some embodiments, the new reference image is derived from the treatment image by subtracting out the hot spot in order to obtain a new reference image resembling those acquired prior to treatment. The hot spot is, in this case, also removed from the estimated temperature map stored along with the new reference image.) Based on the monitored temperature, the treatment may be adjusted (step 424). For example, if the temperature in the region surrounding the target approaches intolerably high levels, the energy applied in subsequent sonications (or other treatment steps) may be reduced.

In some embodiments, image acquisition continues until the temperature in the monitored area has returned to a known temperature distribution, e.g., body temperature. From the phase differences between images taken along and after treatment, it is possible to retroactively compute and/or adjust the thermal maps associated with these images. Such retroactive temperature monitoring can be useful to verify the temperatures measured during treatment and/or alert the treating physician or other system operator to any errors and unexpected events.

As will be apparent to those of skill in the art, the methods described above can be modified in several ways. For example, various method steps may be executed in a different order than described. Moreover, in some embodiments, the steps of acquiring an initial reference library prior to treatment are omitted, and the library is, instead, compiled during treatment by successively adding reference records comprising treatment images (or images derived therefrom) and associated data to the library, beginning with an initially empty library. Further, target tracking and thermometry (e.g., as described above with reference to FIGS. 3 and 4) may be combined in various ways and configurations, e.g., using separate, shared, or partially shared libraries and employing the same or separate image similarity criteria. In embodiments where the methods share a common reference library, for example, each reference record may include a reference/baseline image and, associated therewith, target coordinates and a thermal map. Reference-library extension (e.g., as more generally described with reference to FIG. 2) may also be applied to other imaging methods that utilize a previously compiled reference library during a real-time procedure.

Figure 1:
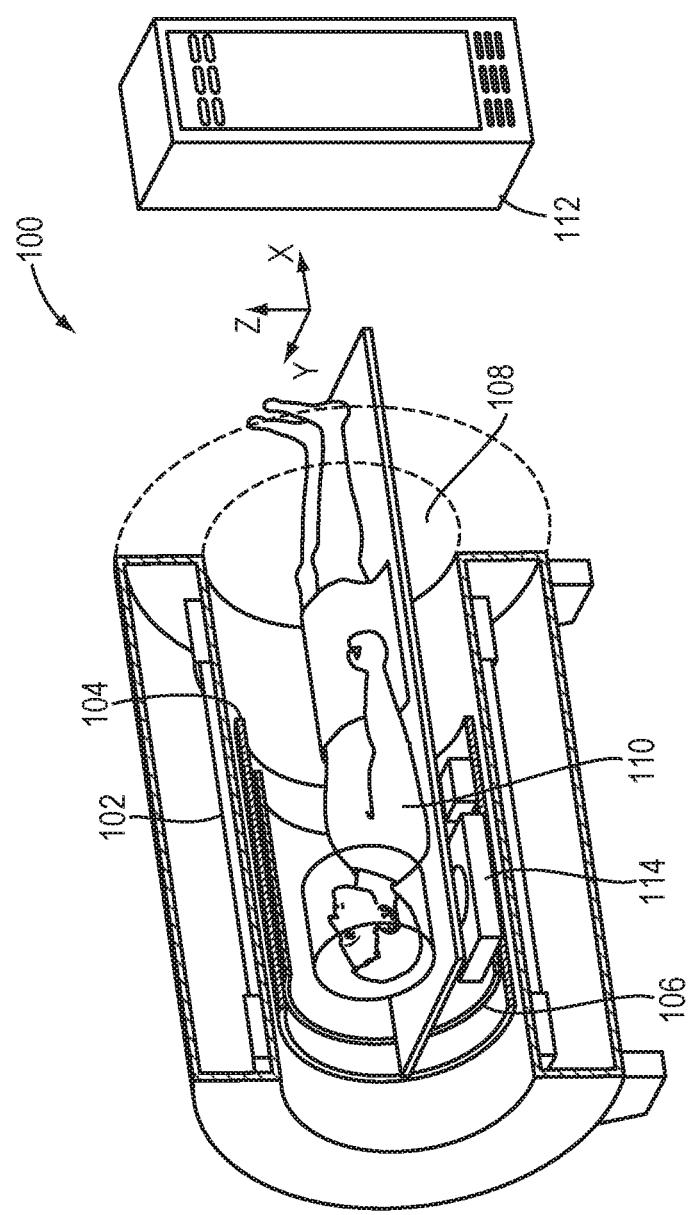
FIG. 1 illustrates an MRI-guided focused ultrasound system in accordance with various embodiments.
Figure 5:
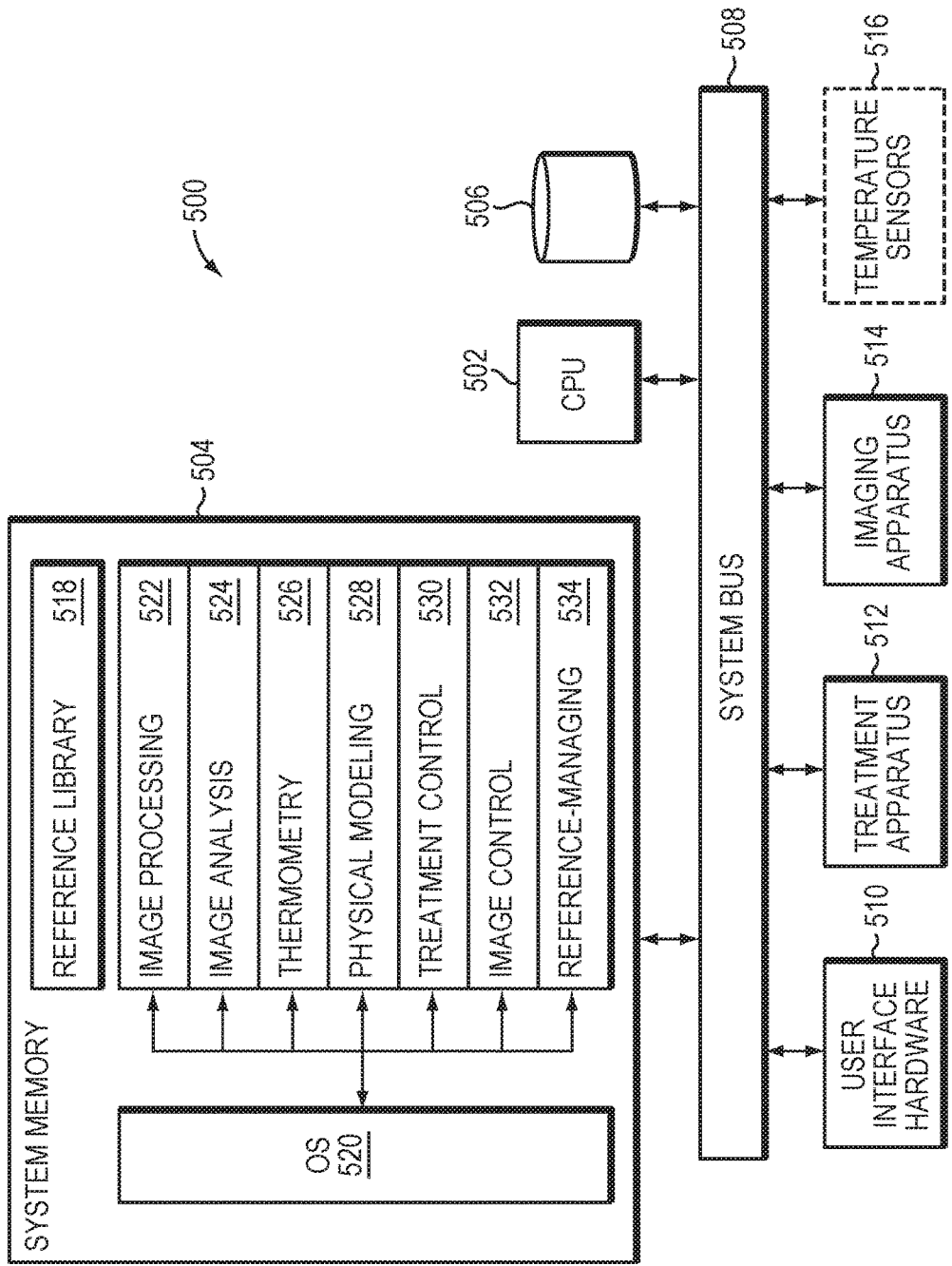
FIG. 5 is a block diagram illustrating an image-processing and control facility implementing methods in accordance with various embodiments.

Various methods in accordance herewith can be implemented using an (otherwise conventional) imaging or image-guided treatment system, such as the MRgFUS system 100 depicted in FIG. 1, in conjunction with a customized image-processing and control facility (e.g., integrated with computation unit 112) in communication with the treatment apparatus (e.g., the beam former setting the phases and amplitudes of an ultrasound transducer array) and the imaging apparatus. The image-processing and control facility may be implemented in any suitable combination of hardware, software, firmware, or hardwiring. FIG. 5 illustrates an exemplary embodiment where the facility is provided by a suitably programmed general-purpose computer 500. The computer includes a central processing unit (CPU) 502, system memory 504, and non-volatile mass storage devices 506 (such as, e.g., one or more hard disks and/or optical storage units). The computer 500 further includes a bidirectional system bus 508 over which the CPU 502, memory 504, and storage devices 506 communicate with each other and with internal or external input/output devices, such as traditional user interface components 510 (including, e.g., a screen, a keyboard, and a mouse) as well as the treatment apparatus 512, the imaging apparatus 514, and (optionally) any temperature sensors 516 facilitating absolute-temperature measurements.

The system memory 504 may store the reference library 518. Alternatively, the library may be stored on the mass storage devices 506, and individual reference records may be loaded into system memory 504 as needed. In some embodiments, each reference record is a data file storing both the (raw and/or real-space) image data and the (application-specific) associated data (such as the target coordinates or an absolute-temperature map). In a modification, the reference record may consist of multiple files, which, however, form an integrated data structure; for example, the record may include a file storing the associated data along with a pointer to the corresponding image file. In some embodiments, the library 518 is stored in the form of a plurality of image files, a plurality of application-specific data files (e.g., thermal maps), and a database linking the images with the corresponding associated information.

The system memory 504 further stores instructions, conceptually illustrated as a group of modules, that control the operation of CPU 502 and its interaction with the other hardware components. An operating system 520 directs the execution of low-level, basic system functions such as memory allocation, file management and operation of mass storage devices 506. At a higher level, one or more service applications provide the computational functionality required for image-processing, the particular imaging application(s) (e.g., motion tracking and/or thermometry), and creation and extension of the reference library 518.

For example, as illustrated, the system may include an image processing module 522 for reconstructing real-space images from raw image data received from the imaging apparatus 514 and performing other general image-processing functions; an image analysis module 524 for extracting locational information of the target and/or other object(s) of interest from the reconstructed reference images; a thermometry module 526 for computing temperature-difference and absolute-temperature maps from the treatment images and the information in the reference library; a physical-modeling module 528 for computationally simulating motion, deformation, and/or temperature evolution in the anatomical region of interest; a treatment-control module 530 for computing and adjusting treatment parameters (such as the desired beam direction and intensity) and controlling the treatment apparatus 512 based thereon (e.g., via computed relative phases between the elements of a phased-array ultrasound transducer); an image-control module 532 for controlling the imaging apparatus 514; and a reference-managing module 534 for measuring similarity between treatment and reference images (whether raw or reconstructed images) and selecting suitable reference images based thereon, as well as for directing the execution of the other modules and controlling process flow as needed for the extension of the reference library in accordance herewith. Of course, the various computational functionalities may be grouped and organized in many different ways, as will be readily apparent to one of skill in the art. The modules (or, generally, processor-executable instructions) may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages; in some embodiments, different modules are programmed in different languages.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method for monitoring an anatomical region during treatment thereof, the method comprising:
   (a) prior to the treatment, establishing a library of reference image records of the anatomical region, each reference image record comprising (i) at least a reference image and (ii) data associated with the reference image including a thermal map corresponding to the reference image;
   (b) during the treatment, repeatedly
      (i) acquiring a treatment image of the anatomical region;
      (ii) comparing a currently acquired treatment image and the reference images in the library based on real-space or k-space image data to determine whether a reference image from the library matches the currently acquired treatment image according to an image-similarity criterion; and (iii) if none of the reference images in the library matches the currently acquired treatment image according to the image-similarity criterion, computationally deforming a treatment thermal map associated with one of previously acquired treatment images and extending the reference library by adding to the library a new reference image record comprising (A) a new reference image and (B) data associated with the new reference image including a new thermal map based at least in part on the deformed treatment thermal map; and (c) monitoring the anatomical region based at least in part on the acquired treatment images and the extended reference library.

2. The method of claim 1, wherein the new reference image satisfies the image-similarity criterion with respect to the treatment image.

3. The method of claim 1, wherein extending the reference library comprises adding the currently acquired treatment image to the library as the new reference image.

4. The method of claim 1, wherein extending the reference library comprises adding an image derived from the currently acquired treatment image to the library as the new reference image.

5. The method of claim 1, wherein extending the reference library comprises estimating motion of an object of interest in the anatomical region based on at least one of the currently acquired treatment image or said one of the previously acquired images, acquiring a new treatment image encompassing the object of interest based on the estimated motion, and adding the new treatment image to the library as the new reference image.

6. The method of claim 1, wherein extending the reference library further comprising deriving corresponding data for the new reference image and adding it to the library in association therewith.

7. The method of claim 6, wherein the data associated with the reference images further comprises respective locations of an object of interest therein.

8. The method of claim 7, wherein the location of the object of interest in the new reference image is derived from the currently acquired treatment image using image analysis.

9. The method of claim 7, wherein the location of the object of interest in the new reference image is derived from said one of the previously acquired treatment images and a physical model characterizing motion of the object of interest.

10. The method of claim 7, wherein monitoring the anatomical region comprises monitoring the location of the object of interest based on the locations stored in association with reference images matching the acquired treatment images.

11. The method of claim 7, wherein the object of interest comprises a treatment target.

12. The method of claim 11, wherein the treatment comprises application of a therapeutic energy beam to the target, the method further comprising adjusting the beam based on the monitored location.

13. The method of claim 6, wherein the data associated with the reference images further comprises respective locations of multiple objects of interest therein, monitoring the anatomical region comprising monitoring locations of the objects of interest based on the locations stored in association with reference images matching the acquired treatment images.

14. The method of claim 13, wherein the objects of interest comprise a treatment target and at least one organ sensitive to therapeutic energy, the treatment comprising application of a therapeutic energy beam to the target, the method further comprising adjusting the beam based on the monitored locations.

15. The method of claim 1, wherein the thermal maps are absolute-temperature maps.

16. The method of claim 1, wherein deformation of the treatment thermal map associated with said one of the previously acquired treatment images is based at least in part on characterization of tissue motion and/or tissue deformation of the anatomical region between the currently acquired treatment image and said one of the previously acquired treatment images.

17. The method of claim 16, wherein deformation of the treatment thermal map associated with said one of the previously acquired treatment images is further based on a computational physical model.

18. The method of claim 17, wherein the computational physical model characterizes at least one of tissue elasticity or temperature evolution in the monitored anatomical region.

19. The method of claim 1, wherein monitoring the anatomical region comprises monitoring a temperature change therein based on phase differences between the acquired treatment images and matching reference images.

20. The method of claim 19, wherein monitoring the anatomical region further comprises monitoring an absolute temperature therein based on the thermal maps stored in association with the reference images matching the acquired treatment images.

21. The method of claim 20, further comprising establishing a thermal map of the anatomical region after treatment, and retroactively adjusting the monitored absolute temperature during treatment based thereon.

22. The method of claim 1, wherein the library is initially empty of reference images.

23. The method of claim 1, wherein the library initially contains a plurality of reference images each corresponding to a different stage of motion of the anatomical region.

24. The method of claim 1, further comprising modifying parameters associated with the treatment based at least in part on the monitoring.

25. The method of claim 24, wherein the parameters comprise at least one of a treatment energy, a treatment power, a treatment beam shape, or a targeted area.

26. The method of claim 1, further comprising changing imaging parameters during the treatment.

27. A system for monitoring an anatomical region during treatment thereof, the system comprising:

(a) an imaging apparatus for imaging the anatomical region;

(b) memory for storing a library of reference image records comprising (i) reference images of the anatomical region and (ii) data associated with the reference images including thermal maps corresponding to the reference images; and (c) a computation unit configured to (i) repeatedly cause the imaging apparatus to acquire a treatment image of the anatomical region during the treatment, (ii) comparing a currently acquired treatment image and the reference images in the library based on real-space or k-space image data to determine whether any of the reference images in the library matches the currently acquired treatment image according to an image-similarity criterion, (iii) if none of the reference images in the library matches the currently acquired treatment image, computationally deforming a treatment thermal map associated with one of previously acquired treatment images and extend the reference library by adding to the library a new reference image record comprising (A) a new reference image and (B) data associated with the new reference image including a new thermal map based at least in part on the deformed treatment thermal map, and (iv) monitor the anatomical region based at least in part on the acquired treatment images and the extended reference library.

28. The system of claim 27, further comprising an ultrasound transducer array for focusing a therapeutic energy beam onto a target in the anatomical region.

29. The system of claim 27, wherein the computation unit is configured to adjust the beam based on the monitoring.

30. The system of claim 27, wherein the computation unit is further configured to derive data corresponding to the new reference image and adding it to the library in association therewith.

31. The system of claim 30, wherein the data associated with the reference images further comprises respective locations of at least one object of interest therein.

32. The system of claim 30, wherein the computation unit is further configured to monitor a location of the at least one object of interest based on the locations stored in association with reference images matching the acquired treatment images.

33. The system of claim 27, wherein the thermal maps are absolute-temperature maps.

34. The system of claim 27, wherein the computation unit is configured to monitor an absolute temperature in the anatomical region based on phase differences between the acquired treatment images and matching reference images and on the thermal maps stored in association with the matching reference images.

35. The method of claim 1, wherein the location of the anatomical region on the reference image comprises spatial coordinates.

36. The system of claim 27, wherein the locations of the anatomical region on the reference images comprise spatial coordinates.

37. The system of claim 27, wherein the computation unit is further configured to computationally deform the treatment thermal map associated with said one of the previously acquired treatment images using a computational physical model.

38. The system of claim 37, wherein the computation unit is further configured to computationally deform the treatment thermal map associated with said one of the previously acquired treatment images based at least in part on characterization of tissue motion and/or tissue deformation of the anatomical region between the currently acquired treatment image and said one of the previously acquired treatment images.

39. The system of claim 37, wherein the computational physical model characterizes at least one of tissue elasticity or temperature evolution in the monitored anatomical region.

40. The system of claim 27, wherein the computation unit is further configured to:
process the currently acquired treatment image so as to remove a hot spot therefrom; and
comparing the processed treatment image and the reference images in the library based on real-space or k-space image data to determine whether any of the reference images in the library matches the processed treatment image according to the image-similarity criterion.

41. The system of claim 27, wherein the computation unit is further configured to:
predict a change in at least one of the reference images resulting from the treatment;
manipulate the at least one of the reference images to reflect the predicted change; and
comparing the currently acquired treatment image and the manipulated reference image based on real-space or k-space image data to determine an image similarity therebetween.

* * * * *